United States Patent [19]

Moucharafieh

[11] Patent Number: 4,931,086

[45] Date of Patent: Jun. 5, 1990

[54] THIOLCARBAMATE-TRIAZINE LIQUID HERBICIDE COMPOSITION

[76] Inventor: Nadim C. Moucharafieh, 939 Lexington, #6, El Cerrito, Calif. 94530

[21] Appl. No.: 102,052

[22] Filed: Sep. 28, 1987

Related U.S. Application Data

[63] Continuation of Ser. No. 920,554, Oct. 20, 1986, abandoned, Continuation-in-part of Ser. No. 354,980, Mar. 5, 1982, abandoned.

[51] Int. Cl.$^5$ .................. A01N 43/66; A01N 43/16
[52] U.S. Cl. ................................ 71/93; 71/88; 71/100; 71/DIG. 1; 71/94; 71/90; 71/118; 71/105; 71/103; 71/95; 71/111; 71/106

[58] Field of Search ............ 71/DIG. 5, 93, 100, 71/88

[56] References Cited

FOREIGN PATENT DOCUMENTS 889274 10/1981 Belgium .
773478 5/1981 South Africa .

*Primary Examiner*—Glennon H. Hollrah
*Assistant Examiner*—Mark W. Russell
*Attorney, Agent, or Firm*—Denis A. Polyn

[57] ABSTRACT

A liquid herbicide composition containing a liquid thiolcarbamate and a solid s-triazine, an antidote compound, an anionic, non-ionic or modified non-ionic emulsifier, a dispersing agent, a wetting agent, anti-forming agent, thickener and water, that is thermally stable and has excellent dilution properties.

4 Claims, No Drawings

THIOLCARBAMATE-TRIAZINE LIQUID HERBICIDE COMPOSITION

This is a continuation, of application Ser. No. 920,544, filed October 20, 1986 now abandoned. Which is a continuation-in-part of application Ser. No. 354,980, filed March 5, 1982 now abandoned.

BACKGROUND OF THE INVENTION

The following thiolcarbamate herbicides are known and correspond to the following general formula:

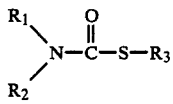

in which
- $R_1$ is $C_1$–$C_6$ alkyl, $C_2$–$C_6$ alkenyl and $C_2$–$C_6$ alkynyl;
- $R_2$ is $C_1$–$C_6$ alkyl, $C_2$–$C_6$ alkenyl, cyclohexyl and phenyl; or
- $R_1$ and $R_2$ together with nitrogen atom to which they are attached form a ring structure having from 4–10 carbon atoms, preferably, piperidino, hexamethyleneimino, decahydroquinolino, 2,5-dimethylpiperidino, or 5-ethyl-2-methylpiperidino;
- $R_3$ is $C_1$–$C_6$ alkenyl, benzyl, phenyl, halophenyl, and methyl substituted phenyl or benzyl, and $C_1$–$C_6$ haloalkyl.

These thiolcarbamate compounds are described in U.S. Pat. Nos. 2,913,327; 3,198,786; 3,185,720; 2,913,324; and 3,846,115.

These thiolcarbamates have been shown particularly effective in the control of grassy type weeds which interfere with the production of a wide variety of crops, e.g., barley, corn, lentils, peanuts, peas, potatoes, soybeans, spinach, tobacco and tomatoes.

Also the following s-triazine herbicides are known and correspond to the following general formula

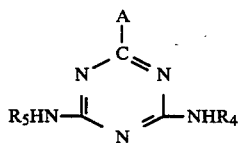

in which
- A is chlorine, methoxy, and methylthio; and
- $R_4$ and $R_5$ are independently $C_1$–$C_4$ alkyl, $C_2$–$C_8$ alkoxyalkyl, and $C_1$–$C_4$ cyanoalkyl.

These compounds are described in U.S. Pat. Nos. 2,891,855 and 2,909,420.

Previously, various s-triazines have been combined with various thiolcarbamates to form a herbicidal composition. (See U.S. Pat. Nos. 3,037,853 and 3,682,616.)

Several recent patents describe liquid formulations containing a liquid thiolcarbamate and a solid s-triazine compound. (See Belgian Patent No. 889,274 and South African Patent Application No. 77/3478.) None of the formulations described in these publications are successful commercially. The solid s-triazine part of the formulation separates from the liquid thiolcarbamate upon standing and therefor is commercially unexceptable. In addition, the prior art formulations have poor dilution properties in hard water and nitrogenous fertilizer solutions.

The present invention is directed to a flowable herbicidal formulation containing one or more liquid thiolcarbamates and one or more solid s-triazines. The formulation is dilutable by water or water-containing liquid before application in the field.

The formulation of this invention has the advantage that it can contain a high amount (50–85 percent by weight) of active ingredients, i.e., the liquid thiolcarbamate and solid s-triazine/herbicides. The formulation is thermally stable over a wide temperature range. The formulation is compatible with and dilutable by both hard and soft water. The formulation is also compatible and dilutable with a nitrogenous fertilizer solution.

Most importantly, neither the solid s-triazine component nor water of the herbicidal formulation of this invention separate from the liquid thiolcarbamate component upon aging over months of storage over a wide temperature range. The formulation has been found to be stable over months of storage over a wide temperature range.

DESCRIPTION OF THE INVENTION

One embodiment of this invention is a novel herbicidal composition comprising:

(a) one or more liquid thiolcarbamates of the formula

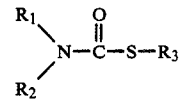

in which
- $R_1$ is $C_1$–$C_6$ alkyl, $C_2$–$C_6$ alkenyl and $C_2$–$C_6$ alkynyl;
- $R_2$ is $C_1$–$C_6$ alkenyl, cyclohexyl and phenyl; or
- $R_1$ and $R_2$ together with the nitrogen atom to which they are attached form a ring structure having from 4–10 carbon atoms, preferably, piperidino, hexamethyleneimino, decahydroquinolino, 2,5-dimethylpiperidino, or 5-ethyl-2-methylpiperidino;
- $R_3$ is $C_1$–$C_6$ alkyl, $C_2$–$C_4$ alkenyl, benzyl, phenyl, halophenyl, and methyl substituted phenyl or benzyl, $C_1$–$C_6$ haloalkyl; preferably $R_1$, $R_2$ and $R_3$ are independently $C_1$–$C_6$ alkyl; most preferably $R_1$ and $R_2$ are each isobutyl, and $R_3$ is ethyl;

(b) one or more solid s-triazine herbicides of the formula

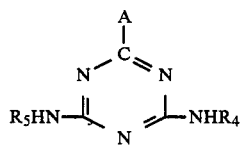

in which
- A is chlorine, methoxy, and methylthio, preferably chlorine; and
- $R_4$ and $R_5$ are independently $C_1$–$C_4$ alkyl, $C_1$–$C_8$ alkoxyalkyl, and $C_1$–$C_4$ cyanoalkyl, preferably $R_4$ and $R_5$ are independently $C_1$–$C_4$ alkyl, more preferably $R_4$ is ethyl, and $R_5$ is isopropyl.

(c) optionally, an an acyl or thioacyl substituted oxazolidine or thiazolidine antidote compound of the formula

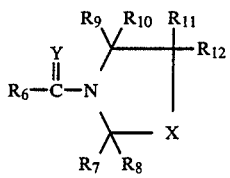

wherein
X is oxygen or sulfur;
Y is oxygen or sulfur;
$R_6$ is $C_1$–$C_{10}$ alkyl, $C_1$–$C_{10}$ haloalkyl, $C_1$–$C_4$ alkylthio, $C_2$–$C_4$ chloralkenyl;
$R_8$, $R_9$, $R_{10}$ and $R_{12}$ are hydrogen, $C_1$–$C_4$ alkyl, $C_2$–$C_4$ alkoxyalkyl, $C_1$–$C_4$ alkylol;
$R_7$ and $R_{11}$ are hydrogen, $C_1$–$C_4$ alkyl, $C_2$–$C_4$ alkoxyalkyl, phenyl, naphthyl, substituted phenyl wherein substituents are monofluoro, monochloro, dichloro, nitro, methyl, methoxy, or hydroxy;
or an amide of haloalkanic acid having 2 through 7 carbon atoms or an amide compound having the formula

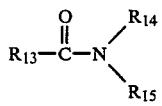

wherein $R_{13}$ can be selected from the group consisting of haloalkyl; haloalkenyl, alkyl; alkenyl; cycloalkyl; cycloalkylalkyl; halogen; hdyrogen; carboalkoxy; N-alkenylcarbamylalkyl; N-alkenylcarbamyl; N-alkyl-N-aklynylcarbamyl; N-alkyl-N-alkynylcarbamylalkyl; N-alkenylcarbamylalkoxyalkyl; N-alkyl-N-alkynylcarbamylalkoxyalkyl; alkynoxy; haloalkoxy, thiocyanatoalkyl; alkenylaminoalkyl; alkylcarboalkyl; cyanoalkyl; cyanatoalkyl; alkenylaminosulfonoalkyl; alkythioalkyl; haloalkylcarbonyloxyalkyl; alkyoxycarboalkyl; haloalkenylcarbonyloxyalkyl; hydroxyhaloalkyloxyalkyl; hydroxyalkylcarboalkyoxyalkyl; hydroxyalkyl; alkoxysulfonoalkyl; furyl, thienyl, alkyldithiolenyl; theinalkyl; phenyl and substituted phenyl wherein said substituents can be selected from halogen, alkyl, haloalkyl, alkoxy, carbamyl, nitro, carboxylic acids and their salts, haloalycarbamyl; phenylalkyl; phenylhaloalkyl; phenylalkenyl; substituted phenylalkenyl whereinsaid said substituents can be selected from halogen, alkyl, alkoxy; halophenoxy; phenylalkoxy; phenylalkylcarboxyalkyl; phenylcycloalkyl; halophenylalkenoxy; halothiophenylalkyl; halophenyloxyalkyl; bicycloalkyl; alkenylcarbamylpyridinyl; alkynylcarbamylpyridinyl; dialkenylcarbamylbicycloalkenyl; alkynylcarbamylbicycloalkenyl, $R_{14}$ and $R_{15}$ can be the same or different and can be selected from the group consisting of alkenyl; haloalkenyl; hydrogen, alkyl, haloalkyl; alkynyl; cyanoalkyl; hydroxyalkyl; hydroxyhaloalkyl; haloalkylcarboxyalkyl; alkylcarboxyalkyl; alkoxycarboxyalkyl; thioalkylcarboxyalkyl; alkoxycarboalkyl; alkylcarbamyloxyalkyl; amino; formyl; haloalkyl-N-alkylamido; haloalkylamido; haloalkylamidoalkyl; haloalkylN-alkylamidoalkyl; haloalkylamidoalkenyl; alkylimino; cycloalkyl; alkylcycloalkyl; alkoxyalkyl; alkylsulfonyloxyalkyl; mercaptoalkyl; alkylaminoalkyl; alkoxycarboalkenyl; haloalkylcarbonyl; alkylcarbonyl; alkenylcarbamyloxyalkyl; cycloalkylcarbamyloxyalkyl; alkoxycarbonyl; haloalkoxycarbonyl; halophenylcarbamyloxyalkyl; cycloalkenyl; phenyl; substituted phenyl wherein said substituents can be selected from alkyl, halogen, haloalkyl, alkoxy, haloalkylamido, phthalamido, hydroxy, alkylcarbamyloxy, alkenylcarbamyloxy, alkylamido, haloalkylamido, alkylcarboalkenyl, phenylsulfonyl; phenylalkyl; substituted phenylalkyl wherein said substituents can be selected from halogen, alkyl; dioxyalkylene, halophenoxyalkylamidoalkyl; alkylthiodiazolyl; piperidylalkyl; thiazolyl; alkylthiazolyl; benzothiazolyl; piperidylalkyl; thiazolyl; alkythioazolyl, benzothioazolyl; halobenzothiazolyl; furylalkyl; pyridyl; alkylpyridyl; alkyloxazolyl; tetrahydrofurylalkyl; 3-cyano, 4,5-polyalkylene-thienyl; α-haloalkylacetamidophenylalkyl; α-haloalkylacetamidonitrophenylalkyl; α-haloalkylacetamidohalophenylalkyl; cyanoalkenyl; $R_{14}$ and $R_{15}$ when taken together can form a structure consisting of piperidinyl; alkylpiperidinyl; alkyltetrahydropyridyl; morpholyl; alkylmorpholyl; azobicyclononyl; benzoalkylpyrrolidinyl; oxazolidyl; alkyloxazolidyl; perhydroquinolyl; alkylaminoalkenyl; provided that when $R_{14}$ is hydrogen $R_{15}$ is other than hydrogen and halophenyl, preferably the antidote compound is N,N-diallyl dichloroacetamide or 2,2,5-trimethyl-N-dichloroacetamide;

(d) an anionic emulsifier having the structural formula

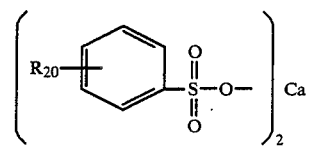

wherein
$R_{20}$ is a $C_{10}$–$C_{15}$ alkyl, preferably a branched-chain dodecyl;

(e) a non-ionic or modified non-ionic emulsifier having the structural formula

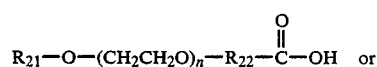

wherein
n is the integer 7 through 14, preferably the integer 9, $R_{21}$ is a hydrophobe of $C_5$–$C_{20}$ alkyl, $C_5C_{20}$ alkylphenyl, $C_5$–$C_{20}$ alkylnaphthyl or the di- or tri- $C_5$–$C_{20}$ alkyl substituted phenyl or naphthyl, preferably $R_{21}$ is the group

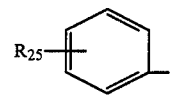

wherein $R_{25}$ is a $C_7$–$C_{12}$ alkyl, preferably nonyl, $R_{22}$ is a methylene, ethylene, or propylene group, preferably methylene;

(f) a water soluble wetting agent having the structural formula

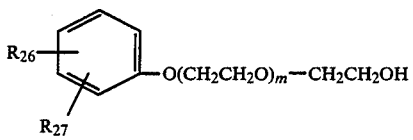

wherein $R_{26}$ is $C_7$–$C_{12}$ alkyl, preferably nonyl, $R_{27}$ is $C_7$–$C_{12}$ alkyl, preferably nonyl or hydrogen and m is the integer 50 through 150, preferably 70–120;

(g) the calcium salt of lignin sulfonate as a dispersing agent;

(h) an anti-foaming agent, preferably dimethylpolysiloxane;

(i) fumed silicas as a thickener; and (j) optionally, water.

Any water-soluble liquid pesticide (or a solution thereof in a water-soluble solvent) can be used in place of the recited liquid thiolcarbamate. Also, any water insoluble, solid pesticide that is substantially insoluble (less than 5%) in the liquid pesticide can be used in place of the recited s-triazine.

The ratio of the liquid thiolcarbamate to the solid s-triazine can range from 1:1 to 12:1 with the total amount of active ingredients varying between 50 to 85 percent by total weight at the 1:1 ratio to between 71.5 to 80.5 percent by total weight at the 12:1 ratio.

The use of a recited antidote compound is optional. Therefore, the amount of antidote that in the composition will be zero when none is desired. When it is desired, the amount can range up to an amount that is herbicidal. This range is termed "an antidotally effective amount." Generally, this range will vary from 0.1 to about 15.0 percent by weight based upon the weight of the thiolcarbamate. Preferably the range is between about 3 to about 5 percent by weight based upon the weight of the thiolcarbamate.

The combined weight of the water-insoluble anionic and non-ionic or modified non-ionic emulisifiers can range between 5.0 to 20.0 percent by weight based upon the total weight of the formulation. Preferably, the amount of the anionic emulsifier can vary from about 15 to about 65 percent by weight of the combined amount. Correspondingly, the non-ionic emulsifier can vary from about 85 to about 35 percent by weight of the combined amount.

The amount of water-soluble wetting agent can range between 2.0 to 5.0 percent by weight per total weight.

The amount of water-soluble dispersing agent can range between 0.5 to 5.0 percent by weight per total weight.

The amount of anti-foaming agent can range between 0.01 to 0.5 percent by weight per total weight.

The amount of water can range from zero to 35.0 percent by weight per total weight.

The amount of the fumed silicas thickener can range between 0.5 to 5.0 percent by weight per total weight.

The pesticidal composition of the invention can be prepared by separately preparing an oil portion and an aqueous portion and then combining the two together along with the thickener.

First considering the aqueous portion, the solid s-triazine herbicide is ground to a particle size of from about 2 to about 5 microns. Preferably grinding is done in water in conventional grinding equipment, i.e., such as a ball mill. The water-soluble wetting and dispersing agents can be combined with the s-triazine either before, during, or after the grinding step. The anti-foaming agent is used during the grinding step to minimize foaming. When water is used in the grinding of the s-triazine, an aqueous slurry of the s-triazine in water results from the grinding step.

The oil portion is prepared by dissolving the anionic, non-ionic or modified non-ionic emulsifier along with any antidote in the liquid thiolcarbamate and any diluent. The solution can be prepared in any convenient vessel. Any stirring apparatus, such as a paddle stirrer, can be used to aid solution. Heating can also be used to aid the solution.

Next, the aqueous portion and the oil portion are combined. Simply, the aqueous portion can be poured into the oil portion using conventional equipment. Simple stirring can be used to form a homogeneous mixture.

Next, the thickener is added to the combined portions to increase the viscosity of the mixture and insure suspension of the s-triazine.

The following are examples of the herbicidal compositions of this invention.

EXAMPLE I

The following ingredients are used in this formulation:

| Ingredient | Weight (grams) |
|---|---|
| (a) S-ethyl N,N-diisobutyl thiolcarbamate | 460.8 |
| (b) 2-chloro-4-ethylamino-4-isopropylamino-1,3,5-triazine (atrazine) | 392.0 |
| (c) N,N-diallyl dichloroacetamide (antidote) | 19.2 |
| (d) calcium salt of dodecyl benzene sulfonate (anionic emulsifier) | 156.1 |
| (e) $C_9H_{19}$—⟨phenyl⟩—$O(CH_2CH_2O)_9$—$CH_2$—$\overset{O}{\overset{\|}{C}}$—OH (non-ionic emulsifier) | 164.0 |
| (f) $C_9H_{19}$—⟨phenyl⟩—$O(CH_2CH_2O)_{99}$—$CH_2CH_2OH$ (wetting agent) | 44.0 |
| (g) calcium salt of lignin sulfonate (dispersing agent) | 24.0 |
| (h) dimethyl polysiolxane (anti-foaming agent) | 0.8 |
| (i) fumed silicas (dispering agent) | 10.0 |
| (j) water | 339.2 |

The liquid portion of the formulation is prepared by weighing the liquid thiolcarbamate, antidote, anionic and non-ionic emulsifiers into a one-quart glass bottle. The bottle is capped, warmed and shaken to yield a clear, homogenous solution.

The aqueous portion of the formulation is prepared by weighing the wetting agent, dispersing agent, anti-foaming agent, water and atrazine (previously air-milled to an average particle size of 3–4 microns) into a two-liter glass beaker. The beaker is fitted with a flexible plastic cover. A high speed dissolver, extending through an opening in the cover down to the bottom of the beaker, is used to blend the ingredients into an aqueous slurry.

The liquid portion (455.0 grams) was weighed into a 4-liter glass beaker. Next, 535.0 g of the resulting aqueous slurry of atrazine is added to the liquid portion of the formulation and 10.0 grams of fumed silicas are added as a suspending agent. The mixture is covered and swirled to wet the components. Finally, a high-speed liquid dissolver is used for about 10 minutes to completely blend all the ingredients.

The resulting product is a homogeneous liquid mixture and remains stable to separation. The product can be diluted with hard and soft water or nitrogenous fertilizer solutions.

EXAMPLE II

The following ingredients are used in this formulation:

| Ingredient | Weight (grams) |
|---|---|
| (a) S-ethyl N,N-diisobutyl thiolcarbamate | 678.40 |
| (b) 2-chloro-4-ethylamino-4-isopropylamino-1,3,5-triazine (atrazine) | 550.00 |
| (c) N,N-diallyl dichloroacetamide (antidote) | 29.04 |
| (d) calcium salt of dodecyl benzene sulfonate (anionic emulsifier) | 45.12 |
| (e) $C_9H_{19}\text{-}C_6H_4\text{-}O(CH_2CH_2O)_9\text{-}CH_2\text{-}C(=O)\text{-}OH$ (non-ionic emulsifier) | 47.44 |
| (f) $C_9H_{19}\text{-}C_6H_4\text{-}O(CH_2CH_2O)_{99}O\text{-}CH_2CH_2OH$ (wetting agent) | 12.10 |
| (g) calcium salt of lignin sulfonate (dispersing agent) | 12.60 |
| (h) dimethyl polysiolxane (anti-foaming agent) | 0.30 |
| (i) fumed silicas (dispering agent) | 61.00 |
| (j) water | 425.00 |

The liquid portion of the formulation is prepared by weighing the liquid thiolcarbamate, antidote, anionic, non-ionic or modified non-ionic emulsifiers into a one-quart glass bottle. The bottle is capped, warmed and shaken to yield a clear, homogenous solution.

The aqueous portion of the formulation is prepared by weighing the wetting agent, dispersing agent, anti-foaming agent, water and atrazine into a half-gallon ceramic ball mill containing one-half inch ceramic balls. The mill is covered and turned on rollers for three days. The average size of the atrazine in the slurry is reduced to about 3–74 microns (measured on a Coulter counter).

The milled slurry (900 g) is poured into a glass tray (12.5×8.5×2.0 inches) and allowed to air dry. The partially dried material is placed in an oven at 90°–100° F. overnight to completely remove the remaining water. A solid material (517.5 g) is obtained.

Next, 372 grams of the dried material was combined with 420 g of the liquid portion and 8.0 g of fumed silicas in a half-gallon ceramic ball mill. The mill was turned for about 3 hours to yield a homogenous suspension of the solid atrazine in the liquid thiolcarbamate.

The resulting product liquid mixture remains stable to separation. The product can be diluted with hard and soft water or nitrogenous fertilizer solutions.

The composition of this invention can be applied by standard tank mix operations using water to dilute the concentrate, or it can be applied by addition to irrigation water supplied to the field. These methods of application permit the penetration of the active composition into the soil as the water is absorbed therein. It is not necessary that the compositions be admixed with the soil particles. After application by the above discussed methods, the wetted top soil can be tilled below the surface to a depth of at least one-half inch by conventional means such as discing, dragging, or mixing.

An herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

A manufacturer of a particular herbicide recommends a range of rates and concentrations calculated to maximize weed control. The range of rates varies from approximately 0.01 to 50 pounds per acre (lb/A) (0.0112 to 56 kilograms per hectare (k/ha)), usually from 0.1 to 25 lb/A (0.112 to 28 k/ha). The actual amount used depends upon several considerations including particular weed suspectibility and overall cost limitations.

Unfortunately, at these rates of application both weeds and the intended crop beneficiary can be injured. Therefore, a particular herbicide's use may be limited by its injurous effect on the cultivated crop.

To preserve the beneficial aspects of herbicide use and to mitigate crop damage, herbicidal antidotes have been developed. These antidotes reduce or eliminate damage to the crop without substantially impairing the ameliorative effect of the herbicide. They are described in U.S. Pat. Nos. 3,989,502, 4,021,224, 4,072,688 and 4,124,372, which are incorporated herein by reference.

Although several explanatory theories have been advanced, the precise mechanism by which an antidote reduces herbicidal injury has not been empirically verified. An antidote compound may in fact by a remedy, interferent, protectant, or antagonist. As used herein "antidote" describes the effect of herbicidal phytoxocity to weed species and reduced or non-phytotoxicity to cultivated crop species.

I claim:
1. A herbicidal composition comprising
"(a) a liquid thiolcarbamate selected from S-ethyl, N,N-diisobutyl thiolcarbamate or S-ethyl N,N-dipropyl thiocarbamate;"
"(b) a solid s-triazine compound selected from atrazine or cyanazine;"
(c) optionally an antidotally effective amount of "N,N-diallyl dichloroacetamide or 2,2,5-trimethyl-3-dichloroacetyl oxazolidine;"

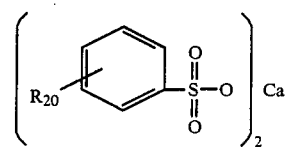

wherein $R_{20}$ is a $C_{10}$–$C_{15}$ alkyl;
(e) a non-ionic or modified non-ionic emulsifier having the structural formula

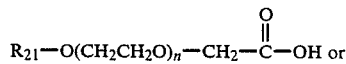 or

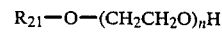

wherein n is the integer 7 through 14 and $R_{21}$ is a hydrophobe of $C_5$–$C_{20}$ alkyl, $C_5$–$C_{20}$ alkylphenyl, $C_5$–$C_{20}$ alkylnaphthyl or the di- or tri- $C_5$–$C_{20}$ alkyl substituted phenyl or naphthyl (f) a water-souble wetting agent that is insoluble in said thiolcarbamate having the structural formula

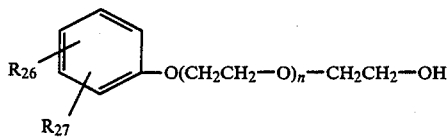

wherein $R_{26}$ is $C_7$–$C_{12}$ alkyl, $R_{27}$ is $C_7$–$C_{12}$ alkyl or hydrogen and m is the integer 50 through 150;

(g) the calcium salt of lignin sulfonate as a dispersing agent;
(h) an anti-foaming agent;
(i) fumed silicas; and
(j) water.

2. The herbicidal composition of claim 1 wherein:
(a) the liquid thiolcarbamate is S-ethyl N,N-diisobutyl thiolcarbamate;
(b) the triazine is atrazine; and
(c) the antidote is N,N-diallyl dichloroacetamide.

3. The herbicidal composition of claim 1 wherein:
(a) the liquid thiolcarbamate is S-ethyl, N,N-diisobutyl thiolcarbamate;
(b) the s-triazine is atrazine;
(c) the antidote is N,N-diallyl dichloroacetamide;
(d) the anionic emulsifier is the calcuim salt of dodecyl benzene sulfonic acid;
(e) the non-ionic or modified non-ionic emulsifier has the structural formula

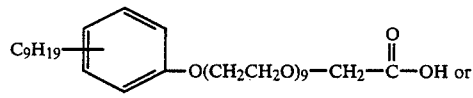

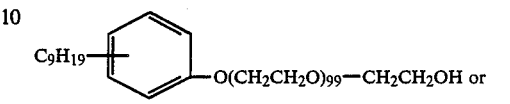

(f) the wetting agent has the structural formula

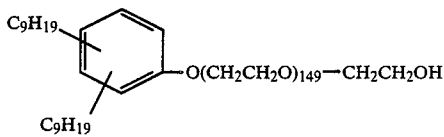

(g) the dispersing agent is the calcium salt of lignin sulfonate
(h) anti-foaming agent;
(i) fumed silica; and
(j) water.

4. The herbicidal composition of claim 1 wherein the non-ionic or modified non-ionic emulsifier has the structural formula

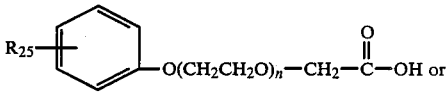

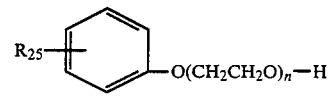

wherein n is the integer 7 through 14 and $R_{25}$ is a $C_7$–$C_{12}$ alkyl.

* * * * *